(12) United States Patent
Okamura et al.

(10) Patent No.: US 6,288,067 B1
(45) Date of Patent: *Sep. 11, 2001

(54) PROPHYLACTIC OR THERAPEUTIC AGENTS FOR DRUG-INDUCED RENAL INJURY

(75) Inventors: Mikio Okamura; Yoshiharu Kanayama, both of Osaka; Junichi Yoshikawa, Hyogo-ken; Haruo Shintaku, Osaka, all of (JP)

(73) Assignee: Suntory Limited, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/427,550

(22) Filed: Oct. 27, 1999

Related U.S. Application Data

(63) Continuation of application No. PCT/JP99/00916, filed on Oct. 27, 1999.

(30) Foreign Application Priority Data

Feb. 27, 1998 (JP) .................................................. 10-048158

(51) Int. Cl.[7] .......................... A61K 31/50; A61K 31/495
(52) U.S. Cl. ...................................... 514/252.16; 514/258
(58) Field of Search ................................ 514/252.16, 258

(56) References Cited

U.S. PATENT DOCUMENTS 4,920,122 * 4/1990 Naruse et al. ........................ 514/254

FOREIGN PATENT DOCUMENTS

| 0 908 182 | 4/1999 | (EP) . |
| 59-25323 | 2/1984 | (JP) . |
| 59-76086 | 4/1984 | (JP) . |
| 61-277618 | 12/1986 | (JP) . |
| 002157755 | 3/1994 | (JP) . |
| 63-267781 | 11/1998 | (JP) . |
| WO 92/07566 | 5/1992 | (WO) . |

OTHER PUBLICATIONS

Fukushima, et al. "Analysis of Reduced Forms of Biopterin in Biological Tissues and Fluids", Analyticial Biochemistry 102, (1980) pp., 176–188.

R.M.J. Palmer, et al. "Nitric oxide release accounts for the biological activity of endothelium–derived relaxing factor", Nature 327, (1987) pp. 524–526.

Kwon, et al., "Reduced Biopterin as a Cofactor in the Generation of Nitrogen Oxides by Murine Macrophages", J. Biol. Chem., (1989) 264(34) pp. 20496–20501.

Bobadilla, et al. "Role of nitric oxide in real hemodynamic abnormalities of cyclosporin nephrotoxicity", Kidney Int. 46, (1994) pp. 773–779.

Medical Practice, vol. 14, No. 8, (1997) pgsz 1273–1275.

"ZINZOUGAKU" Approach freom renal pathophysiology, ed. Kurokawa, K. Nankoudou, (1995) pp. 419–428.

Bune, et al., Inhibition of Tetrahydrobiopterin Synthesis Reduces Nitric Oxide Production by Isolated Glomeruli in Immune Complex Glomerulonephritis, *Experimental Nephrology*, 1996, vol. 4, pp. 43–47.

Gardner et al., Clinically Relevant Doses and Blood Levels Produce Experimental Cyclosporine Nephrotoxicity When Combined with Nitric Oxide Inhibition, *Transplantation*, 1996, vol. 61, pp. 1506–1512.

Bune et al., Inhibition of Tetrahydrobiopterin Synthesis Reduces in Vivo Nitric Oxide Production in Experimental Endotoxic Shock, *Biochemical and Biophysical Research Communications*, 1996, vol. 220, pop. 13–19.

* cited by examiner

*Primary Examiner*—Frederick Krass
(74) *Attorney, Agent, or Firm*—Pillsbury Winthrop LLP

(57) ABSTRACT

It is an object of the present invention to provide a pharmaceutical composition for effectively preventing or improving drug-induced renal injury. The present invention provides pharmaceutical composition for preventing or treating drug-induced renal injury, comprising as an active ingredient a compound of the formula (I):

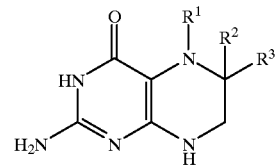

wherein $R^1$ and $R^2$ each represents a hydrogen atom or taken together with each other represent a single bond, while $R^3$ represents —CH(OH)CH(OH)CH$_3$, —CH(OCOCH$_3$)CH(OCOCH$_3$)CH$_3$, —CH$_3$, —CH$_2$OH or a phenyl group when $R^1$ and $R^2$ each represents a hydrogen atom, or —COCH(OH)CH$_3$ when $R^1$ and $R^2$ together represent a single bond, or a pharmaceutically acceptable salt thereof.

6 Claims, No Drawings

PROPHYLACTIC OR THERAPEUTIC AGENTS FOR DRUG-INDUCED RENAL INJURY

This is a continuation of: PCT/JP99/00916 filed Oct. 27, 1999.

BACKGROUND OF THE INVENTION

The present invention relates to pharmaceutical compositions for preventing and/or treating drug-induced renal injury, comprising as an active ingredient a compound of the formula (I):

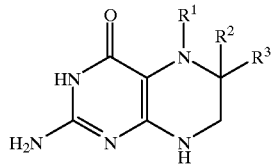

wherein $R^1$ and $R^2$ each represents a hydrogen atom or taken together with each other represent a single bond, while $R^3$ represents —CH(OH)CH(OH)CH$_3$, —CH(OCOCH$_3$)CH(OCOCH$_3$)CH$_3$, —CH$_3$, —CH$_2$OH or a phenyl group when $R^1$ and $R^2$ each represents a hydrogen atom, or —COCH(OH)CH$_3$ when $R^1$ and $R^2$ together represent a single bond, or a pharmaceutically acceptable salt thereof.

Clinically, drug-induced renal injury is principally manifested as nephrotic syndrome (or proteinuria in milder cases) and renal dysfunction. For example, glomerulopathy represented by membranous neuropathy induced by gold drugs is manifested as nephrotic syndrome, while tubular disorder induced by nephrotoxic agents represented by cisplatin is manifested as acute renal failure. Transport disorder specifically occurring in the renal tubules presents with clinical conditions such as Fanconi syndrome, renal tubular acidosis, renal diabetes insipidus, etc. Acute interstitial nephritis induced by methicillin or the like is manifested as renal dysfunction. Thus, drug-induced renal injury presents with various clinical conditions dependent on the type of the drug or the affected site (Medical Practice, vol. 14, No. 8, 1997, p. 1273).

For example, cyclosporin A is an immunosuppressive agent commonly used during transplantation, but causes renal injury at an incidence of 50% or more dependent on the blood concentration of the drug because of its high nephrotoxicity. Renal injury induced by cyclosporin A has various phenotypes including acute renal failure, chronic renal failure, hemolytic uremic syndrome, thrombotic microangiopathy, hypertension, electrolyte imbalance (such as hyperkalemia, metabolic acidosis, hypomagnesemia), etc. Acute renal failure is required to be identified by renal biopsy due to the difficulty in discriminating the condition from acute rejection. A decreased glomerular filtration rate (GFR) during the early stage of administration is attributed to-enhancement of the renin-angiotensin system, stimulation of the sympathetic nerve system, increased production of thromboxane A$_2$ and the effect of endothelin. On the other hand, patients with renal transplants often develop chronic renal failure caused by long-term administration of cyclosporin, which is difficult and sometimes impossible to discriminate from chronic rejection even by renal biopsy. Tissue injury induced by cyclosporin mainly involve endothelial cells disorder ranging from interlobar artery to afferent arterioles wherein said tissue injury principally cause renal sclerosis, interstitial cell invasion and fibrosis. Moreover, hypomagnesemia often occurs during cyclosporin administration, and extreme hypomagnesemia may cause systemic seizure under the influence of cyclosporin ("ZINZOUGAKU", Approach from Renal Pathophysiology, ed. Kurokawa, K., Nankodo, pp. 419–428, 1995).

Vascular endothelium has been known to play an important role in vascular tonus or thrombopoiesis, and in 1980 the presence of endothelium-derived relaxing factor (EDRF) was first reported. The entity of EDRF was proved to be nitric oxide (NO) in 1987. NO is a gaseous radical and has been shown to readily pass through cell membranes and have a wide variety of effects such as circulation control, neurotransmission, inhibition of platelet aggregation, antibacterial or anticancer effect. NO not only controls metabolism by reacting with heme enzyme or SH enzyme groups, but also has physiological functions and pathological activity by crosstalking with active oxygen species such as superoxide ($O_2^-$), SH compounds, ascorbic acid or the like. However, its in vivo molecular entity is still unknown in many respects because all of these molecules are unstable.

NO having a wide variety of effects as described above is produced when L-arginine is oxidized from $N^G$-hydroxyl-L-arginine into L-citrulline and the reaction is catalyzed by an enzyme called NO synthase (NOS). NOS has isoforms including vascular endothelial-type, cerebellar-type, and inducible-type. The vascular endothelial-type mainly exists in the vascular endothelium and kidney, while the cerebellar-type exists in the nervous system. The inducible-type exists in macrophages or the like induced during inflammation or tissue injury. The gene for each of these isoforms has already been cloned and structurally analyzed. As a result, the gene for NOS was found to contain a binding site for (6R)-L-erythro-5,6,7,8-tetrahydrobiopterin (hereinafter referred to as "BH4") included in compounds of the formula (I) as active ingredients of the present invention, in addition to those for coenzymes such as calmodulin (CaM), flavin, NADPH. Moreover, BH4 has been suggested to actually be involved in control of the function of NOS.

Thus, the vasorelaxing effect of NO and the control of NOS functions by BH4 have been somewhat known. However, the relationship of effects of NO and NOS activity with drug-induced renal injury has not been explained, and nothing has been known about the relationship between drug-induced renal injury and endogenous BH4.

The purpose of preventing or treating drug-induced renal injury is not only to prevent or treat renal injury but also to permit the use of drugs responsible for renal injury so that patients may enjoy a prolonged and higher quality of life. However, any improvement in diseases or conditions of drug-induced renal injury can not be expected at present, because acute renal failure requires discontinuation of drug administration in order to allow renal function to recover and chronic renal failure requires dialysis or renal transplantation. Thus, no therapy for drug-induced renal injury has been established yet and neither a prophylactic or therapeutic agent therefor exists at present. As a result, drugs which are completely satisfactory in terms of side effects, safety during long-term use and improvement in QOL (quality of life) are in great demand.

Thus, therapeutic agents satisfying truly desirable conditions are required, and the development of prophylactic agents having a renal protective action is also in great demand.

The compounds of the formula (I) as active ingredients in pharmaceutical compositions of the present invention are known compounds for use in therapeutic agents against malignant hyperphenylalaninemla, depression, Parkinson's disease, etc. For example, see Japanese Patent Public Disclosure (KOKAI) Nos. 25323/84, 76086/84, 277618/86 and 267781/88.

SUMMARY OF THE INVENTION

It is an object of the present invention to provide a safe pharmaceutical composition for drug-induced renal injury without side effects, which improves circulation and organic functions by controlling the functions of endothelial cells, retards the progress of complications and improves the quality of life of patients.

The inventors have found abnormal functions of NOS in cyclosporin-induced renal injury rats prepared as a model of drug-induced renal injury. The inventors also have found an increased NOS activity level and an increased BH4 level in said cyclosporin-induced renal injury rats. As a result of various studies, we unexpectedly have found that BH4 administration recovers the functions of endothelial cells and normalizes the functions of NOS to give physiologically very natural and excellent renal protective effects, and thus accomplished the present invention. Accordingly, the present invention relates to effective prevention or treatment with BH4 preparations for drug-induced renal injury.

DETAILED DESCRIPTION OF THE INVENTION

The present invention relates to a pharmaceutical composition for preventing or treating drug-Induced renal injury, comprising as an active ingredient a compound of the formula (I):

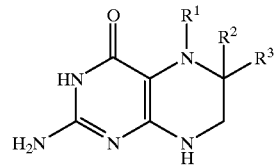

wherein $R^1$ and $R^2$ each represents a hydrogen atom or taken together with each other represent a single bond, while $R^3$ represents —CH(OH)CH(OH)CH$_3$, —CH(OCOCH$_3$)CH(OCOCH$_3$)CH3, —CH$_3$, —CH$_2$OH or a phenyl group when $R^1$ and $R^2$ each represents a hydrogen atom, or —COCH(OH)CH$_3$ when $R^1$ and $R^2$ together represent a single bond, or a pharmaceutically acceptable salt thereof.

As used herein, the term drug-induced renal injury includes pathologic states of the kidney associated with lesions caused by drugs. Clinically, drug-induced renal injury is principally manifested as nephrotic syndrome (or proteinuria in milder cases) and renal dysfunction. Drug-induced renal injury as used herein includes those caused by a lowered renal function, those aggravated by a lowered renal function, those for which cure is retarded by a lowered renal function, etc. Clinical states of drug-induced renal injury are mainly classified into acute renal failure such as prerenal acute renal failure, intrinsic acute renal failure and postrenal acute renal failure, and chronic renal failure or end-stage renal failure with progressed renal dysfunction. Intrinsic acute renal failure may induce diseases such as angiitis, glomerular lesion, acute glomerulonephritis, rapidly progressive glomerulonephritis, hemolytic uremic syndrome, malignant hypertension, renal cortical necrosis, disseminated intravascular coagulation, scleroderma, acute interstitial nephritis, nephrotic syndrome or acute pyelonephritis. Different tissue lesions are observed dependent on the affected site. For example, arterioles are involved by arteriolostenosis, endothelial disorder, arteriolothrombosis; glomerulus are involved by membranous neuropathy; tubules and interstitial regions are involved by tubular necrosis, tubular dysfunction, acute interstitial nephritis, tubular emphraxis.

Drugs which may induce drug-induced renal injury are not specifically limited herein. Any drugs may induce renal injury, including but not limited to antibiotics (e.g., penicillin, mitomycin, cyclosporin, amphotericin B, methicillin, cephalosporin, aminoglycoside), non-steroidal anti-inflammatory drugs (NSAID), anti-tumor agents (e.g., cisplatin, ifosfamide, methotrexate), gold drugs, heavy metals (mercury), contrast media, agrichemicals (e.g., Paracort).

When administered to patients with drug-induced renal injury, BH4 can prevent or treat these diseases by recovering the lowered function of endothelial cells to normalize the functions of NOS.

Compounds of the formula (I) as active Ingredients of the present Invention include the following ones and pharmaceutically acceptable salts thereof:

(6R)-L-erythro-5,6,7,8-tetrahydrobiopterin (BH4)

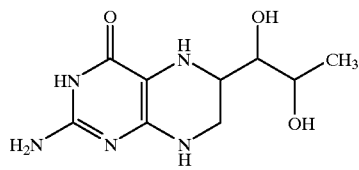

(6R,S)-5,6,7,8-tetrahydrobiopterin, 1',2'-diacetyl-5,6,7,8-tetrahydrobiopterin

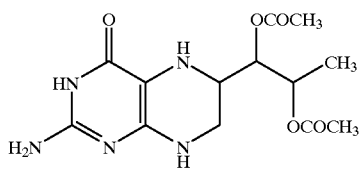

sepiapterin

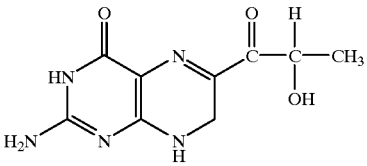

6-methyl-5,6,7,8-tetrahydropterin

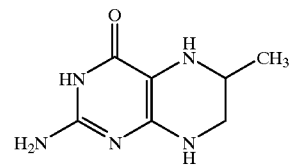

6-hydroxymethyl-5,6,7,8-tetrahydropterin

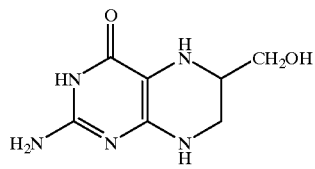

6-phenyl-5,6,7,8-tetrahydropterin

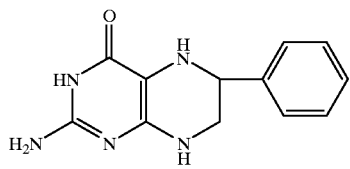

Among the afore-mentioned compounds, 5,6,7,8-tetrahydrobiopterins or salts thereof are preferable, and BH4 or salts thereof are the most preferable.

Compounds of the formula (I) used as active ingredients in the present invention are known compounds. For example, see Japanese Patent Public Disclosure (KOKAI) Nos. 25323/84, 76086/84, 277618/86 and 267781/88. These compounds may be used as appropriate salts with pharmacologically non-toxic acids, including mineral acids such as hydrochloric acid, phosphoric acid, sulfuric acid, boric acid; and organic acids such as acetic acid, formic acid, maleic acid, fumaric acid, mesylic acid.

Pharmaceutical compositions of the present invention are effective against the above mentioned diseases. Namely, they are widely applied to pathologic states of the kidney with lesions caused by drugs.

Pharmaceutical compositions of the present invention are prepared by formulating a compound of the formula (I) with a pharmaceutically common carrier by conventional procedures into a dosage form suitable for oral, rectal or parenteral administration (including administration into vein and cerebrospinal fluid).

The carrier used for these pharmaceutical formulations generally includes excipients, binders, disintegrators, etc. depending on the dosage form chosen.

Typical examples of excipients include starch, lactose, sucrose, glucose, mannitol, cellulose, and examples of binders include polyvinylpyrrolidone, starch, sucrose, hydroxypropylcellulose, and Arabic gum. Examples of disintegrators include starch, agar, gelatin powder, cellulose, CMC, but any other conventional excipients, binders and disintegrators may also be used.

In addition to such carriers, pharmaceutical compositions of the present invention may also contain antioxidants for stabilizing active ingredients. Antioxidants can be appropriately selected from those commonly used for pharmaceutical preparations, such as ascorbic acid, N-acetylcysteine, L-cysteine, dl-α-tocopherol, natural tocopherol etc. They are used in an amount that stabilizes (one or more) active ingredients, and generally they are preferably used in the ratio of 0.2 to 2.0 parts by weight to 1 part by weight of the active ingredient(s).

Formulations of the present invention suitable for oral administration may be provided in the form of tablets, sublingual tablets, capsules, powders, granules or fine granules, or suspensions in a non-aqueous liquid such as emulsions, potions or syrups, that contain the prescribed amount of (one or more) active ingredients.

For example, granules are prepared by homogeneously mixing (one or more) active ingredients with one or more auxiliary ingredients such as carriers and antioxidants as mentioned above, followed by granulation and sieving to uniform grain size. Tablets can be prepared by compacting or molding (one or more) active ingredients optionally with one or more auxiliary ingredients. Capsules are prepared by filling powder or granules of (one or more) active ingredients optionally mixed homogenously with one or more auxiliary ingredients into appropriate capsules using a capsule filling machine or the like. Formulations for renal administration can be provided as suppositories using conventional carriers such as cacao butter. Parental formulations can be provided as dry solids of (one or more) active ingredients sealed in a nitrogen-filled sterilized container. Such dry solid preparations can be administered to patients by dispersing or dissolving them into a determined amount of sterilized water just prior to administration.

These formulations may preferably be prepared by incorporating antioxidants as mentioned above optionally with one or more auxiliary ingredients selected from buffers, flavors, surfactants, thickeners, lubricants, etc. in addition to active ingredients and ordinary carriers.

The dosage of active ingredients, i.e. compounds of the formula (I) may naturally vary with the administration route, the symptom to be treated and the particular patient, and may be ultimately determined by an attendant physician.

For example, an appropriate dosage for treating drug-induced renal injury depends on the purpose of administration, the age, weight, condition of the patient, etc., but ranges from 0.1 to 50 mg/kg (body weight)/day, typically 0.5 to 10 mg/kg (body weight)/day for oral administration.

A desired dosage of said active ingredients may be administered once a day or may be administered in divided doses of two to four times a day at appropriate intervals.

Active ingredients may be administered alone without being mixed with other ingredients, or in combination with pharmaceutical formulations containing other active ingredients suitable for the disease under treatment to facilitate control of the dosage, for example.

In addition to compounds of the formula (I) as active ingredients, formulations of the present invention may contain at least one auxiliary active ingredient selected from the group consisting of substrates or coenzymes or cofactors for NOS such as L-arginine, flavins (for example, FAD, FMN, etc.) and calcium. More excellent therapeutic effects can be expected when compounds of the formula (I) are mixed with these active ingredients than when used alone. The proportion of each of said auxiliary active ingredients in formulations of the present invention is not specifically limited. For example, the weight ratio of at least one selected from L-arginine, flavins and calcium to 1 part by weight of the compounds of the formula (I) may be within the range from 0.1 to 10, preferably 0.5 to 2.

For example, an appropriate dosage of such mixed formulations for treating drug-induced renal injury depends on the purpose of administration, the age, weight, condition of the patient, etc., but ranges from 0.1 to 50 mg/kg (body weight)/day, preferably 0.5 to 10 mg/kg (body weight)/day in terms of the total amount of active ingredients for oral administration.

A physician may appropriately choose formulations containing compounds of the formula (I) alone or in combination with other active ingredients, depending on the age, condition or other factors of the patient.

The most preferable active ingredients used in the present invention are (6R)-L-erythro-5,6,7,8-tetrahydrobiopterin (BH4) and salts thereof, but their analogues such as (6R,S)-5,6,7,8-tetrahydrobiopterin, 1',2'-diacetyl-5,6,7,8-tetrahydrobiopterin, sepiapterin, 6-methyl-5,6,7,8-tetrahydropterin, 6-hydroxymethyl-5,6,7,8-tetrahydropterin or 6-phenyl-5,6,7,8-tetrahydropterin and salts thereof may also be used. Needless to say, however, BH4 naturally occurring component in living bodies is preferable. BH4 dihydrochloride exhibits little toxicity in rats as shown by the acute toxicity of 2 g/kg (body weight) or more via oral route. An optically inactive analogue, (6R,S)-5,6,7,8-tetrahydrobiopterin is also only slightly toxic as reported in Japanese Patent Public Disclosure No. 25323/84 for the treatment of Parkinson's disease, so that it can also be used for the therapy according to the present invention. Other compounds of the formula (I) also exhibit little or no acute toxicity.

The following examples further illustrate the present invention in detail without, however, limiting the same thereto.

EXAMPLES

Example 1

Granules and Fine Granules

To 1 part (by weight) of polyvinylpyrrolidone (Kollidon 30) dissolved in sterilized purified water were added 10 parts of ascorbic acid and 5 parts of L-cysteine hydrochloride to give a homogeneous solution, and then 10 parts of BH4 dihydrochloride were added to prepare a homogeneous solution.

This solution was added to 59 parts of an excipient (mannitol or lactose) and 15 parts of a disintegrator [corn starch or hydroxypropylcellulose (LH-22)], and the mixture was kneaded, granulated, dried, then sieved.

Example 2

Tablets

The homogeneous solution of an active ingredient prepared in Example 1 was mixed with 58 parts of lactose and 15 parts of microcrystalline cellulose, then with 1 part of magnesium stearate and tableted.

Example 3

Capsules

The dosage form prepared in Example 1 was filled into capsules. However, the formulation further contains 0.2% of magnesium stearate as a lubricant.

Example 4

Injection

| BH4 dihydrochloride | 1.5 g |
|---|---|
| Ascorbic acid | 1.5 g |
| L-cysteine hydrochloride | 0.5 g |
| Mannitol | 6.5 g |

The above ingredients were dissolved into sterilized purified water to make 100 ml and sterilized, and each of 1 ml or 2 ml aliquot was dispensed into a vial or ampule, then lyophilized and sealed.

Example 5

Injection

A solution of 2.0 g of BH4 dihydrochloride dissolved in sterilized purified water to make 100 ml under an anaerobic atmosphere was sterilized and sealed in the same way as in Example 4.

Example 6

Suppositories

| BH4 dihydrochloride | 150 parts |
|---|---|
| Ascorbic acid | 150 parts |
| L-cysteine hydrochloride | 50 parts |

The above ingredients were homogeneously ground and dispersed into 9950 parts of cacao butter.

Example 7

Granules

| BH4 dihydrochloride | 5 parts |
|---|---|
| Ascorbic acid | 5 parts |
| L-cysteine hydrochloride | 2 parts |

The above ingredients were used to prepare a homogeneous solution.

This solution was added to a homogeneous mixture of 55 parts of mannitol, 1 part of polyvinylpyrrolidone, 14 parts of hydroxypropylcellulose and 5 parts of L-arginine or calcium, and the mixture was kneaded, granulated, dried, then sieved.

Example 8

Granules

| BH4 dihydrochloride | 5 parts |
|---|---|
| Ascorbic acid | 5 parts |
| L-cysteine hydrochloride | 5 parts |
| Mannitol | 52 parts |
| Polyvinylpyrrolidone (Kollidon 30) | 1 part |
| Hydroxypropylcellulose (LH-22) | 12 parts |
| L-arginine or calcium | 10 parts |

The above ingredients were granulated and sieved in the same way as in Example 7.

Example 9

Granules

| BH4 dihydrochloride | 5 parts |
|---|---|
| Ascorbic acid | 5 parts |
| L-cysteine hydrochloride | 2 parts |

The above ingredients were used to prepare a homogeneous solution.

This solution was added to a homogeneous mixture of 10 parts of L-arginine or calcium, 50 parts of mannitol, 1 part of polyvinylpyrrolidone (Kollidon 30) and 9 parts of hydroxypropylcellulose (LH-22), and the mixture was kneaded, granulated, dried, then sieved.

Example 10

Sprague-Dawley rats at the age of 8 to 10 weeks (supplied from Charles River) (300 g) were divided into the following three experimental groups, and examined by comparison. The animals were grown with a low-salt (0.05%) feed during the experimental period of 6 weeks, and treated for 5 weeks from the second to last weeks of the experiment as follows.
1) CyA Group:
Cyclosporin 15 mg/kg (body weight)/day (subcutaneously administered in admixture with olive oil), n=8.
2) BH4 Group:
Cyclosporin 15 mg/kg (body weight)/day (subcutaneously administered in admixture with olive oil)+BH4 dihydrochloride 10 mg/kg (body weight)/day (orally administered), n=8.
3) Control Group:
Olive oil alone, n=6.

Each group was observed during the experimental period of 6 weeks. The blood pressure, renal cortical NOS activity and blood BP level were determined by the procedures described below. After 6 weeks, blood was collected from the abdominal aorta under anesthesia with phenobarbital, and then the kidney was perfused with physiological saline, then extracted and histologically examined for the effects of BH4 administration on cyclosporin-induced renal injury.
Measurement of Blood Pressure Blood pressure was measured by the tail-cuff method at the start of the experiment and after 2, 4 and 6 weeks.
Measurement of Renal Cortical NOS Activity NOS activity was determined by measuring $^3$H-citrulline produced by renal tissue NOS using 3H-arginine.
Measurement of BP in Blood At the end of observation, HPLC analysis was performed according to the procedure of Fukushima and Nixon (Anal. Biochem. 102: 176–188, 1980) to measure biopterin (BP), a metabolite of BH4. The effects of BH4 administration are examined on the basis of BP level in blood.
Renal Histochemistry Sections were prepared from frozen renal tissues and stained with NADPH-diaphorase for evaluating NOS activity on the tissues. The tissues were also stained with a monoclonal antibody against the macrophage cell membrane antigen ED-1 to examine the NOS isoform.
Histopathological Findings After collecting urine and measuring blood pressure at week 6, the animals were abdominally incised under anesthesia, bled from the abdominal aorta and perfused with physiological saline via this site. The extracted kidney was fixed in a 10% formaldehyde solution, embedded in paraffin, then sliced by a microtome into renal tissue samples of 4 μm. The samples were stained with hematoxylin/eosin (HE) and periodic acid-Shiff. The incidences of pathological findings, i.e. arteriolopathy in the rat renal tissue samples were examined by comparison.
Statistics Group-to-group statistic analyses were made by two-way ANOVA. In the following analyses, the significance level was p<0.05.
Results Blood pressure was kept at a normal level in both of CyA and BH4 groups similarly to control group until the end of observation.

As to renal cortical NOS activity, CyA group showed a significant increase of 260.814 mmol/day (average) as compared with control group. While BH4 group showed an increase of 140.600 mmol/day (average) as compared with control group.

As to blood BP level, CyA group showed a significant increase (of 0.006 nmol (average) as compared with control group). However, BH4 group showed a decrease (of 0.002 nmol (average) as compared with CyA group).

Renal histochemistry showed a lowered NADPH-diaphorase stainability and many invasions of ED-1-positive cells in CyA group. However, BH4 group recovered the NADPH-diaphorase stainability and normalized the functions of vascular endothelial NOS as shown by decreased invasions of ED-1-positive cells.

The incidences of histopathological findings in renal tissue samples are shown in Table 1. BH4 group significantly (p<0.0001) inhibited arteriolopathy, which significantly (p<0.0001) appeared in CyA group.

TABLE 1

| Percentage (%) of the incidence of pathological findings in renal tissues | |
|---|---|
| | Arteriolopathy |
| Control group | 0.00 ± 0.00 |
| CyA group | 74.300 ± 1.767 (SE) |
| BH4 group | 36.814 ± 2.093 (SE) |

In conclusion, histopathological findings of arteriolopathy were observed in CyA group of said model rats. The same group also showed an increase in macrophage-derived inducible NOS activity level. However, orally administered BH4 remarkably improved histopathological findings and increased vascular endothelial NOS activity level, showing that BH4 is useful for the treatment of drug-induced renal injury by recovering the functions of endothelial cells to normalize the functions of NOS.

As has been explained, the present invention provides pharmaceutical compositions that effectively prevent and/or improve drug-induced renal injury. In addition, active ingredients of pharmaceutical compositions of the present invention have no danger of side effects or the like even under long-term use because they inherently occur in living bodies.

What is claimed is:

1. A method for preventing or treating drug-induced renal injury, comprising administering to a patient in need thereof a pharmaceutical composition comprising a compound of the formula (I):

$$\begin{array}{c}\text{(structure shown)}\end{array}$$

wherein $R^1$, and $R^2$ each represents a hydrogen atom or taken together with each other represent a single bond, while $R^3$ represents —CH(OH)CH(OH)CH$_3$, —CH(OCOCH$_3$)CH(OCOCH$_3$)CH$_3$, —CH$_3$, —CH$_2$OH or a phenyl group when $R^1$ and $R^2$ each represents a hydrogen atom, or —COCH(OH)CH$_3$ when $R^1$ and $R^2$ together represent a single bond, or a pharmaceutically acceptable salt thereof.

2. A method of preventing or treating drug-induced renal injury according to claim 1, wherein $R^3$ is L-erythro-CH(OH)CH(OH)CH$_3$.

3. A method of preventing or treating drug-induced renal injury according to claim 1, which is for preventing or treating acute renal failure.

4. A method of preventing or treating drug-induced renal injury according to claim 2, which is for preventing or treating acute renal failure.

5. A method of preventing or treating drug-induced renal injury according to claim 1, which is for preventing or treating chronic renal failure.

6. A method of preventing or treating drug-induced renal injury according to claim, which is for preventing or treating chronic renal failure.

\* \* \* \* \*

UNITED STATES PATENT AND TRADEMARK OFFICE
CERTIFICATE OF CORRECTION

PATENT NO.        : 6,288,067 B1
APPLICATION NO. : 09/427550
DATED             : September 11, 2001
INVENTOR(S)      : Mikio Okamura et al.

It is certified that error appears in the above-identified patent and that said Letters Patent is hereby corrected as shown below:

Column 10, line 61, delete ",".

Column 12, line 5, delete "claim" and insert -- claim 2 --.

Signed and Sealed this

Fourth Day of November, 2008

JON W. DUDAS
*Director of the United States Patent and Trademark Office*